United States Patent
Mochizuki

(10) Patent No.: US 10,882,764 B2
(45) Date of Patent: Jan. 5, 2021

(54) FLUID STERILIZATION APPARATUS

(71) Applicant: NIKKISO CO., LTD., Tokyo (JP)

(72) Inventor: Hiroaki Mochizuki, Hakusan (JP)

(73) Assignee: NIKKISO CO., LTD., Tokyo (JP)

( * ) Notice: Subject to any disclaimer, the term of this patent is extended or adjusted under 35 U.S.C. 154(b) by 0 days.

(21) Appl. No.: 16/567,409

(22) Filed: Sep. 11, 2019

(65) Prior Publication Data

US 2020/0002191 A1 Jan. 2, 2020

Related U.S. Application Data

(63) Continuation of application No. PCT/JP2018/016341, filed on Apr. 20, 2018.

(30) Foreign Application Priority Data

Jun. 6, 2017 (JP) .................................. 2017-111845

(51) Int. Cl.
*C02F 1/32* (2006.01)

(52) U.S. Cl.
CPC ............ *C02F 1/32* (2013.01); *C02F 2301/04* (2013.01); *C02F 2303/04* (2013.01)

(58) Field of Classification Search
None
See application file for complete search history.

(56) References Cited

U.S. PATENT DOCUMENTS

| 5,244,585 A * | 9/1993 | Sugimoto .............. B01D 29/33 210/798 |
| 5,725,762 A * | 3/1998 | Beal ................... B01D 21/0003 110/221 |
| 10,000,396 B1 * | 6/2018 | Preiss ....................... C02F 1/78 |
| 10,293,072 B2 * | 5/2019 | Taghipour ............... A61L 9/205 |
| 2003/0141457 A1 * | 7/2003 | Nakagawa ............. B01J 19/129 250/436 |

(Continued)

FOREIGN PATENT DOCUMENTS

| CN | 203269618 U | 11/2013 |
| CN | 105967271 A | 9/2016 |

(Continued)

OTHER PUBLICATIONS

Preliminary Report on Patentability and a Written Opinion with an English Language Translation which corresponds to Application No. PCT/JP2018/016341; dated Dec. 10, 2019.
Chinese Office Action dated Aug. 4, 2020 in CN Application No. 201880018054.7 (23 pages).

*Primary Examiner* — Andrew Smyth
(74) *Attorney, Agent, or Firm* — Muncy, Geissler, Olds & Lowe, P.C.

(57) ABSTRACT

A fluid sterilization apparatus includes: a flow passage tube in which a processing passage where a passing fluid is sterilized is formed; a first light source that irradiates the processing passage with ultraviolet light; an inflow passage formed in a direction that intersects an outer circumferential surface of the flow passage tube; and a communication passage that causes the inflow passage to communicate with the processing passage. The communication passage has a narrow passage in the middle of a path from the inflow passage toward an opening of a first end, the narrow passage being narrower than a passage toward the inflow passage.

4 Claims, 11 Drawing Sheets

(56) References Cited

U.S. PATENT DOCUMENTS

| | | | | |
|---|---|---|---|---|
| 2005/0040091 | A1* | 2/2005 | Nilsen | C02F 1/38 |
| | | | | 210/198.1 |
| 2008/0203004 | A1* | 8/2008 | Abe | C02F 1/325 |
| | | | | 210/205 |
| 2008/0282749 | A1* | 11/2008 | Hahm | D06F 39/007 |
| | | | | 68/17 R |
| 2015/0129776 | A1* | 5/2015 | Boodaghians | C02F 1/325 |
| | | | | 250/432 R |
| 2016/0045841 | A1* | 2/2016 | Kaplan | B01D 3/06 |
| | | | | 429/49 |
| 2016/0176727 | A1* | 6/2016 | Younis | B01J 19/2405 |
| | | | | 422/24 |

FOREIGN PATENT DOCUMENTS

| | | | | |
|---|---|---|---|---|
| DE | 3924349 | A1 * | 1/1991 | C02F 1/325 |
| JP | H03207364 | A | 9/1991 | |
| JP | 2003514557 | A | 4/2003 | |
| JP | 2009273967 | A * | 11/2009 | |
| JP | 2010125417 | A * | 6/2010 | |
| JP | 2011016074 | A | 1/2011 | |
| JP | 6080937 | B1 | 6/2017 | |
| WO | WO-2016-156877 | A1 | 10/2016 | |

\* cited by examiner

FLUID STERILIZATION APPARATUS

RELATED APPLICATION

The present application is a continuation application of International Application No. PCT/JP2018/016341, filed Apr. 20, 2018, which claims priority to Japanese Patent Application No. 2017-111845, filed Jun. 6, 2017. The entire contents of these applications are incorporated herein by reference.

BACKGROUND OF THE INVENTION

1. Field of the Invention

The present invention relates to a fluid sterilization apparatus.

2. Description of the Related Art

It is known that ultraviolet light has sterilization capability. Devices that radiate ultraviolet light are used for sterilization in medical and food processing fronts. Devices that sterilize a fluid such as water continuously by irradiating the fluid with ultraviolet light are also used. One example is a device in which an ultraviolet LED is provided on the inner wall at a pipe end of a flow passage formed by a straight metal pipe (see, for example, patent document 1).

[patent document No. 1] JP2011-16074

Problem to be Solved by the Invention

In the aforementioned structure where the ultraviolet LED is provided at the end of the straight tube passage, an entrance or an exit that extends in a direction intersecting the axial direction of the flow passage is provided so that a disturbance is produced in the flow of the fluid in the vicinity of the entrance or the exit. In order to irradiate the fluid with ultraviolet light with a high efficiency, it is desired that the state of flow in the flow passage be controlled properly and the ultraviolet light is radiated in a manner suited to the state of flow.

SUMMARY OF THE INVENTION

In this background, one illustrative purpose of the present invention is to provide a technology that approximates the flow in the flow passage to a desired state.

BRIEF DESCRIPTION OF THE DRAWINGS

Embodiments will now be described, by way of example only, with reference to the accompanying drawings that are meant to be exemplary, not limiting, and wherein like elements are numbered alike in several figures, in which.

DETAILED DESCRIPTION OF THE INVENTION

Figure 1:
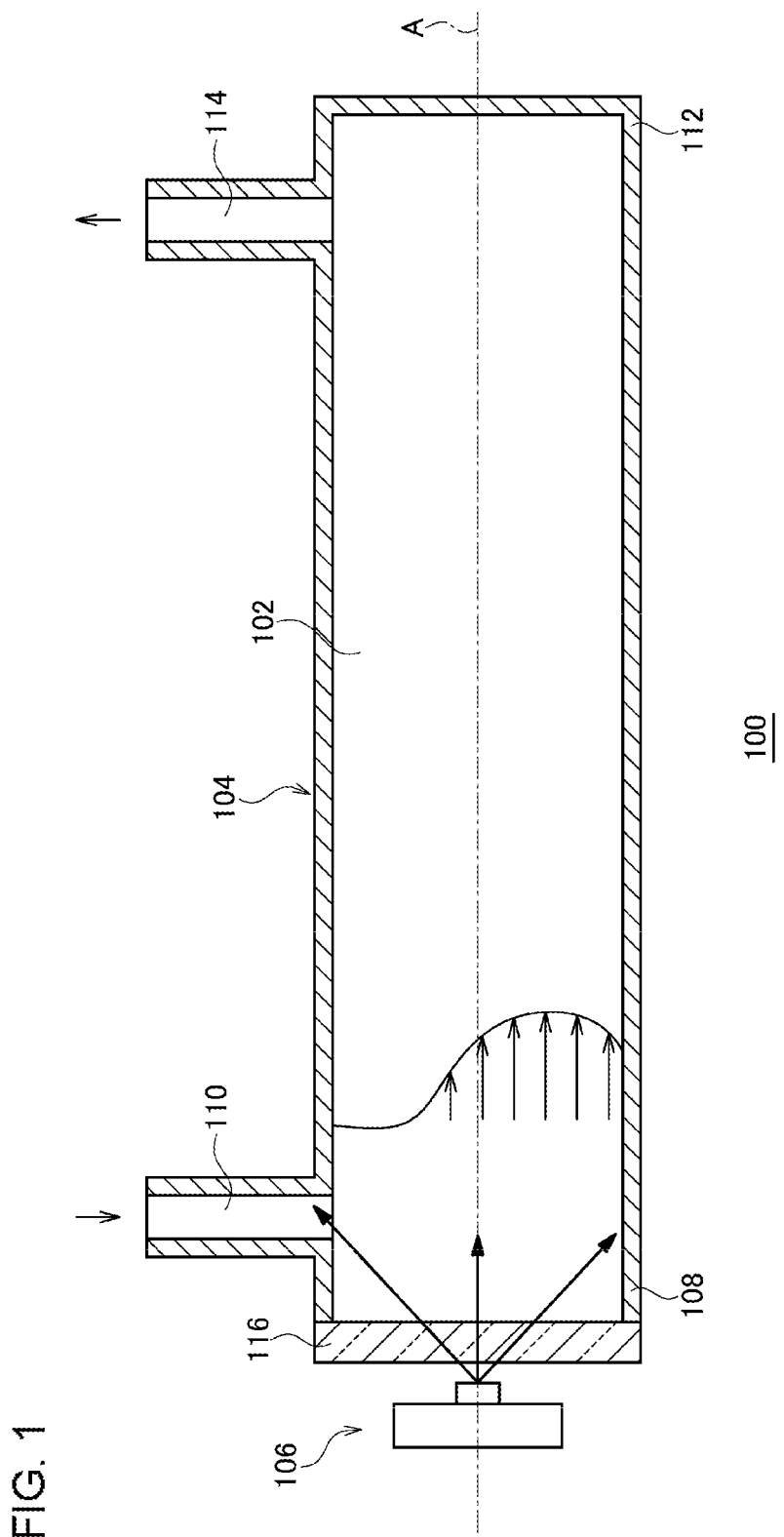
FIG. 1 is a cross-sectional diagram schematically showing a configuration of a fluid sterilization apparatus according to a comparative example.

A fluid sterilization apparatus according to an embodiment includes: a flow passage tube in which a processing passage where a passing fluid is sterilized is formed; a light source that irradiates the processing passage with ultraviolet light; an inflow passage or an outflow passage formed in a direction that intersects an outer circumferential surface of the flow passage tube; and a communication passage that causes the inflow passage or the outflow passage to communicate with the processing passage. The communication passage has a narrow passage in the middle of a path from the inflow passage or the outflow passage toward an opening of one end of the flow passage tube, the narrow passage being narrower than a passage toward the inflow passage or the outflow passage.

According to this embodiment, the narrow passage straightens the flow by blocking a direct flow from the inflow passage toward the one end of the flow passage tube and distributing the flow elsewhere. In particular, the narrow passage inhibits a disturbance from being produced in the flow near the one end of the flow passage tube close to the light source, thereby straightening the flow.

The communication passage may be formed between the flow passage tube and a housing that covers an opening of the one end of the flow passage tube and the outer circumferential surface near the opening. Thus, by designing the shape of a plurality of members properly, the communication passage can be formed as a gap between the plurality of members.

For example, a convex part may be formed more toward the opening than a portion of the outer circumferential surface of the flow passage tube facing the inflow passage or the outflow passage, and the narrow passage may be formed between the convex part and an inner circumferential surface of the housing. In this way, the narrow passage can be formed by forming a simple shape in the flow passage tube.

The convex part may be formed annularly in a circumferential direction of the outer circumferential surface of the flow passage tube. This can condition the flow of the fluid over the entire outer circumference of the flow passage tube.

The housing may be configured such that a convex part is formed more toward opening than an area on an inner circumferential surface of the housing where the inflow passage or the outflow passage is formed, and a narrow passage may be formed between the convex part and the outer circumferential surface of the flow passage tube. In this way, the narrow passage can be formed by forming a simple shape in the flow passage tube.

The convex part may be formed annularly in a circumferential direction of the inner circumferential surface of the housing. This can condition the flow of the fluid over the entire outer circumference of the flow passage tube.

The flow passage tube may be configured such that a concave part is formed in a portion of the outer circumferential surface of the flow passage tube facing the inflow passage or the outflow passage. In this way, an area adjacent to the concave part can be configured as a narrow passage by forming a simple shape in the flow passage tube.

The concave part may be formed annularly in a circumferential direction of the outer circumferential surface of the flow passage tube. This can condition the flow of the fluid over the entire outer circumference of the flow passage tube.

The narrow passage may be provided more toward an opening of the flow passage tube than the concave part. This can condition the flow of the fluid between the concave part and the opening.

The communication passage may have a U-shaped passage that connects a flow of the fluid in a first direction along the outer circumferential surface of the flow passage tube with a flow of the fluid in a second direction opposite to the first direction along the processing passage. This can mitigate a disturbance produced in the flow in the processing passage and condition the flow in the processing passage more successfully than when a communication port is directly provided in the flow passage tube.

The fluid sterilization apparatus may further include: an outflow tube or an inflow tube that forms the outflow passage or the inflow passage. The outflow tube or the inflow tube may be mounted on an opening formed on an outer circumferential surface of the housing and may be supported so as to be rotatable relative to the housing around a center of the opening. This allows the fluid sterilization apparatus to be installed in an orientation in which the device can exhibit its performance easily by changing the orientation of the inflow tube or the outflow tube depending on the location where the fluid sterilization apparatus is installed.

The housing may be mounted on one end of the flow passage tube such that the housing is rotatable around a center of an opening of the flow passage tube. This allows the fluid sterilization apparatus to be installed in an orientation in which the device can exhibit its performance easily by changing the orientation of the inflow tube or the outflow tube depending on the location where the fluid sterilization apparatus is installed.

Another embodiment also relates to a fluid sterilization apparatus. The device includes: a flow passage tube in which a processing passage where a passing fluid is sterilized is formed; a light source that irradiates the processing passage with ultraviolet light; an inflow passage or an outflow passage formed in a direction that intersects an outer circumferential surface of the flow passage tube; and a regulatory passage provided in an area facing an exit of the inflow passage or an entrance of the outflow passage and configured to change a flow of the fluid in a predetermined direction. The regulatory passage has a curved passage leading from the exit of the inflow passage or the entrance of the outflow passage toward an end of the flow passage tube. The regulatory passage has a narrow passage in the middle of a path from the inflow passage or the outflow passage toward one end of the flow passage tube, the narrow passage being narrower than a passage toward the inflow passage or the outflow passage.

According to this embodiment, the narrow passage straightens the flow by blocking a direct flow from the inflow passage toward the one end of the flow passage tube and distributing the flow elsewhere. In particular, the narrow passage inhibits a disturbance from being produced in the flow near the one end of the flow passage tube close to the light source, thereby straightening the flow.

Optional combinations of the aforementioned constituting elements, and implementations of the invention in the form of methods, apparatuses, and systems may also be practiced as additional modes of the present invention.

A description will be given of an embodiment of the present invention with reference to the drawings. In the explanations of the figures, the same elements shall be denoted by the same reference numerals, and duplicative explanations will be omitted appropriately. The configuration described below is by way of example only and does not limit the scope of the present invention.

Comparative Example

A description will first be given of a fluid sterilization apparatus according to a comparative example. FIG. 1 is a cross-sectional diagram schematically showing a configuration of a fluid sterilization apparatus 100 according to a comparative example.

The fluid sterilization apparatus 100 includes a straight tube 104 defining a processing passage 102 and a light source 106 for irradiating the interior of the straight tube 104 with ultraviolet light. An inflow passage 110 extending in the radial direction of the straight tube 104 is provided at one end 108 and an outflow passage 114 extending in the radial direction of the straight tube 104 is provided at the other end 112. A window 116 for transmitting the ultraviolet light from the light source 106 is provided on the one end 108.

In the fluid sterilization apparatus 100, the fluid flowing in from the inflow passage 110 flows in the processing passage 102 in the axial direction of the straight tube 104 and flows out from the outflow passage 114. The inflow passage 110 is directly provided on the side of the straight tube 104 so that a disturbance in the flow of the fluid is produced in the vicinity of the one end 108. More specifically, in the fluid flowing in from the inflow passage 110, the flow toward the side wall of the straight tube 104 facing the inflow passage 110 is predominant. In the interior of the processing passage 102, the speed of the fluid flowing near the side wall facing the inflow passage 110 is relatively higher.

As shown in FIG. 1, this results in an asymmetrical speed distribution with respect to the central axis A of the straight tube 104, which makes it difficult to cause the ultraviolet light from the light source 106 to affect the fluid efficiently. Further, the fluid sterilization apparatus 100 is configured such that a portion of the ultraviolet light output from the light source 106 can travel directly to the inflow passage 110. Therefore, the ultraviolet light is likely to leak from the inflow passage 110.

Thus, the fluid sterilization apparatus according to the following embodiments are devised in view of the fluid sterilization apparatus 100 according to the comparative example.

First Embodiment

Figure 2:
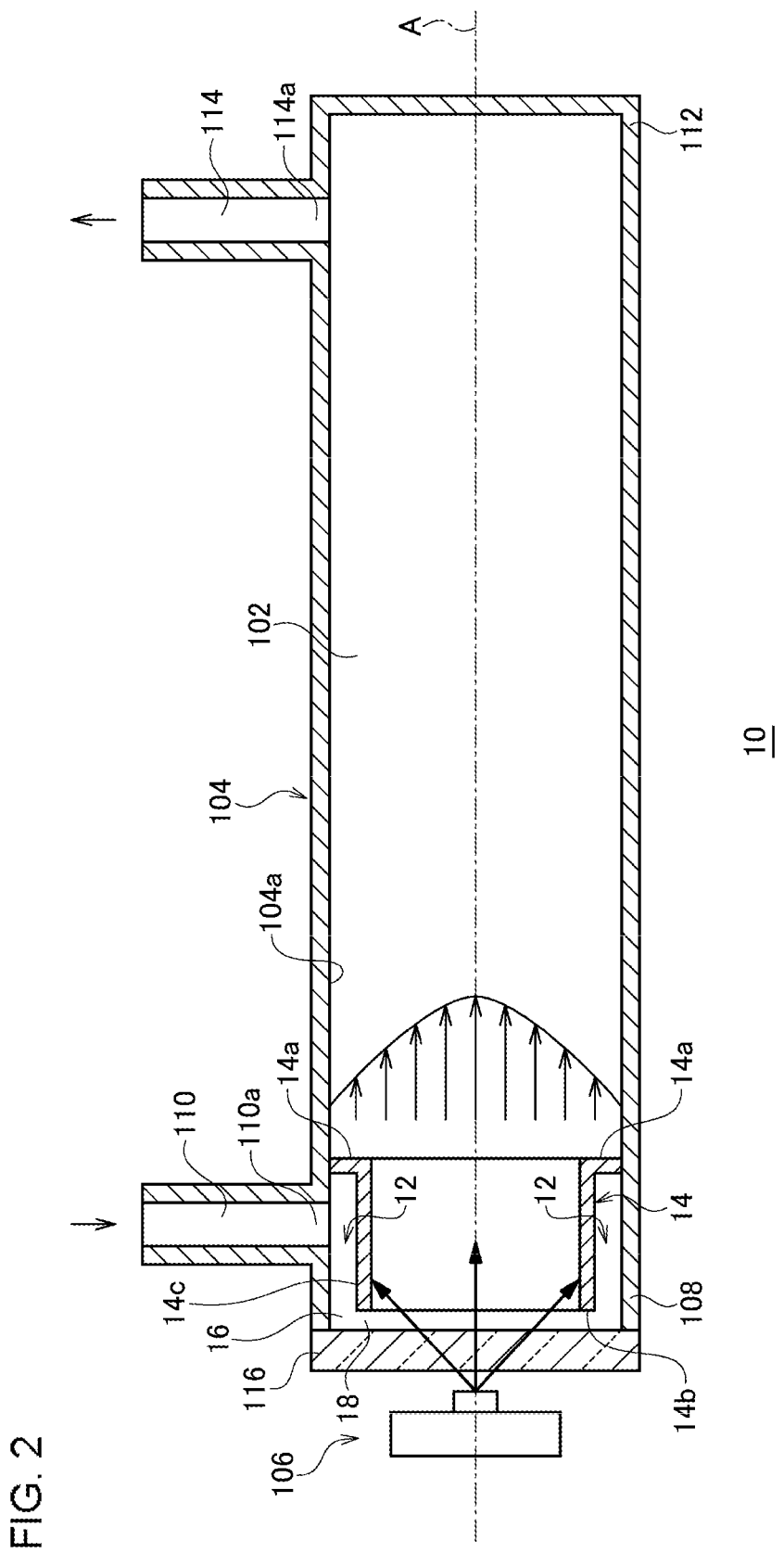
FIG. 2 is a cross-sectional view schematically showing a configuration of a fluid sterilization apparatus according to the first embodiment.

FIG. 2 is a cross-sectional view schematically showing a configuration of a fluid sterilization apparatus according to the first embodiment. Those features that are equivalent to the features of FIG. 1 are denoted by the same reference numerals and a description thereof is omitted as appropriate.

A fluid sterilization apparatus 10 according to the first embodiment includes: a straight tube 104 as a flow passage tube in which a processing passage 102 where the passing fluid is sterilized is formed; a light source 106 that irradiates the processing passage 102 with ultraviolet light; an inflow passage 110 and an outflow passage 114 formed in a direction that intersects the outer circumferential surface of the straight tube 104; and a regulatory passage 12 provided in an area facing an exit 110a of the inflow passage 110 and configured to change the flow of the fluid in a predetermined direction.

The regulatory passage 12 according to this embodiment is an area defined by a cylindrical member 14 formed with a flange 14a at one end face thereof and an inner circumferential surface 104a of the straight tube 104. The regulatory passage 12 has a curved passage 16 leading from the exit 110a of the inflow passage 110 toward one end 108 of the straight tube 104. The regulatory passage 12 has a narrow passage 18 in the middle of a path from the inflow passage 110 toward the one end 108 of the straight tube 104, the narrow passage 18 being narrower than a passage toward the inflow passage.

In the fluid sterilization apparatus 10 according to this embodiment, the narrow passage 18 straightens the flow by blocking a direct flow from the inflow passage 110 toward the one end 108 of the straight tube 104 and distributing the flow elsewhere. In particular, the narrow passage inhibits a disturbance from being produced in the flow near the one end 108 of the straight tube 104, which is close to the light source 106, thereby straightening the flow.

The narrow passage 18 according to the embodiment is formed between a window 116 and an annular other end face 14b of the cylindrical member 14 opposite to the one end face provided with the flange 14a. However, the location of the narrow passage 18 is not limited to the illustrated location. For example, a narrow passage may be formed in the middle of the regulatory passage 12 by providing a convex part in the inner circumferential surface 104a of the straight tube 104 or in an outer circumferential surface 14c of the cylindrical member 14. Alternatively, the regulatory passage 12 according to the embodiment may be provided in an area facing an entrance 114a of the outflow passage 114. The regulatory passage 12 according this embodiment is such that the cross section thereof perpendicular to the axial direction of the straight tube 104 defines an annular area along the outer circumferential surface 14c of the cylindrical member 14. Alternatively, the regulatory passage 12 may define an arc shape or another shape formed only in the vicinity of the area facing the exit 110a of the inflow passage 110 or the entrance 114a of the outflow passage 114.

Second Embodiment

Figure 3:
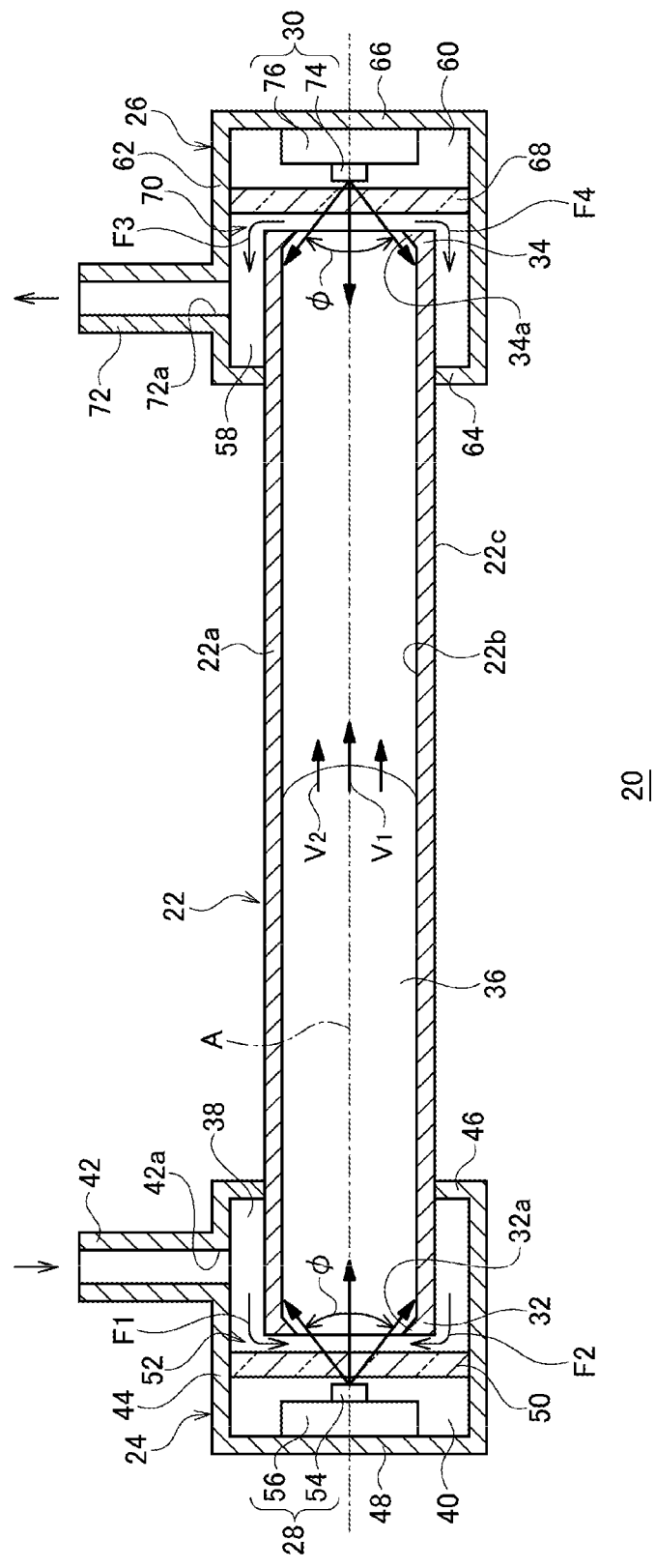
FIG. 3 is a cross-sectional view schematically showing a configuration of a fluid sterilization apparatus according to a second embodiment.

FIG. 3 is a cross-sectional view schematically showing a configuration of a fluid sterilization apparatus 20 according to a second embodiment. The fluid sterilization apparatus 20 includes a flow passage tube 22, a first housing 24, a second housing 26, a first light source 28, and a second light source 30. The first light source 28 and the second light source 30 radiate ultraviolet light toward the interior of the flow passage tube 22. The fluid sterilization apparatus 20 is used to irradiate the fluid (water etc.) flowing in the flow passage tube 22 with ultraviolet light so as to sterilize the fluid.

In this specification, the longitudinal direction of the flow passage tube 22 may be referred to as "axial direction" to facilitate understanding. For example, referring to FIG. 3, the direction parallel to the central axis A is the axial direction. The direction perpendicular to the axial direction may be referred to as the radial direction, and the direction encircling the axial direction may be referred to as the circumferential direction. With reference to the positions at the ends (a first end 32 and a second end 34) of the flow passage tube 22, the direction toward the interior of the flow passage tube 22 may be referred to as "inward" and the direction toward the outside of the flow passage tube 22 may be referred to as "outward".

The flow passage tube 22 is a straight tube comprised of a cylindrical side wall 22a. The flow passage tube 22 has a first end 32 and a second end 34 opposite to the first end 32 and extends in the axial direction from the first end 32 to the second end 34. Ultraviolet light from the first light source 28 is incident on the first end 32 and ultraviolet light from the second light source 30 is incident on the second end 34. The flow passage tube 22 defines a processing passage 36 in which a fluid is irradiated with ultraviolet light.

The flow passage tube 22 is made of a metal material or a resin material. The flow passage tube 22 is desirably made of a material having a high ultraviolet reflectivity. For example, an inner circumferential surface 22b is made of mirror-polished aluminum (Al) or polytetrafluoroethylene (PTFE), which is a fully fluorinated resin. By forming the flow passage tube 22 using a material like the above, the ultraviolet light emitted by the first light source 28 and the second light source 30 can be reflected by the inner circumferential surface 22b to propagate in the longitudinal direction of the flow passage tube 22. In particular, PTFE is a chemically stable material and has a high ultraviolet reflectivity for ultraviolet light and so is suitable as the material for the flow passage tube 22 forming the processing passage 36.

The flow passage tube 22 includes a first projection 32a projecting radially inward from the first end 32 and a second projection 34a projecting radially inward from the second end 34. The first projection 32a and the second projection 34a are formed on the entire circumference of the first end 32 or the second end 34 and are shaped to reduce the inner diameter of the flow passage tube 22. The first projection 32a and the second projection 34a may be shaped such that the amount of projection in the radial direction varies progressively in the axial direction. The first projection 32a and the second projection 34a may have a triangular cross-sectional shape in the cross-section including the central axis A as illustrated.

The first projection 32a and the second projection 34a are formed in a range that does not block the incidence of the ultraviolet light directly output from the first light source 28 or the second light source 30. For example, the first projection 32a and the second projection 34a are formed so as not to block the ultraviolet light in the range of directivity angle half-power beam width $\varphi$ of the first light source 28 or the second light source 30. By providing the first projection 32a and the second projection 34a, a portion of the ultraviolet light reflected or scattered by the inner circumferential surface 22b of the flow passage tube 22 and traveling toward the outside of the flow passage tube 22 is reflected by the first projection 32a or the second projection 34a and returned to the interior of the flow passage tube 22.

The first housing 24 is provided to encircle the first end 32 and defines a first straightening chamber 38 and a first light source chamber 40. The first housing 24 is made of a metal material or a resin material. It is desirable that the first housing 24 be made of a material having a low reflectivity for the ultraviolet light emitted by the first light source 28 and be made of a material having a lower ultraviolet reflectivity than the flow passage tube 22. The first housing 24 may be made of a material that absorbs the ultraviolet light from the first light source 28. By configuring the first housing 24 by using a material like the above, the ultraviolet light from the first light source 28 is inhibited from being reflected by the inner surface of the first housing 24 and leaking outside via an inflow tube 42.

The first housing 24 has a first side wall 44, a first inner end wall 46, and a first outer end wall 48. The first side wall 44 is a cylindrical member extending from the first inner end wall 46 to the first outer end wall 48 in the axial direction and is provided at a position coaxial with the central axis A of the flow passage tube 22. The first inner end wall 46 is a member extending radially outward from the side wall 22a of the flow passage tube 22 to the first side wall 44 and has an annular shape (doughnut shape). The first inner end wall 46 is provided at a position axially inward from the first end 32 and is fixed to an outer circumferential surface 22c of the flow passage tube 22. The first outer end wall 48 is a disc-shaped member provided at a position axially outward from the first end 32. Therefore, the first inner end wall 46 and the first outer end wall 48 are provided at positions axially facing each other, sandwiching the first end 32.

A first window 50 for transmitting the ultraviolet light from the first light source 28 is provided inside the first housing 24. A portion or the entirety of the first window 50 is made of a material having a high ultraviolet transmittance such as quartz ($SiO_2$), sapphire ($Al_2O_3$), and amorphous fluororesin. The first window 50 partitions the interior of the first housing 24 into the first straightening chamber 38 and the first light source chamber 40. The first straightening chamber 38 is an area defined by the first side wall 44, the first inner end wall 46, and the first window 50 and is an area provided annularly to encircle the first end 32 from outside in the radial direction. The first light source chamber 40 is an area defined by the first side wall 44, the first outer end wall 48, and the first window 50 and is provided with the first light source 28.

The first window 50 is an facing member that faces the first end 32 in the axial direction and is provided in the vicinity of the first end 32 so as to provide a first gap 52 of a small dimension relative to the first end 32. For example, the first gap 52 is formed to be narrower than the cross-sectional area of flow of the first straightening chamber 38. It is preferable that the first window 50 be provided such that the dimension of the first gap 52 is uniform over the entire circumference of the first end 32. It is also preferable that the end face of the first end 32 and the face of the first window 50 facing the first end 32 are substantially parallel. Configuring the first gap 52 to be uniform over the entire circumference straightens the flow of the fluid traveling from the first straightening chamber 38 to the processing passage 36 via the first gap 52 and mitigates a disturbance in the flow produced in the vicinity of the first end 32 of the processing passage 36.

The first housing 24 is provided with an inflow port 42a and an inflow tube 42. The inflow port 42a is a communication port through which the fluid irradiated with ultraviolet light in the processing passage 36 flows in and is provided at a position communicating with the first straightening chamber 38. For example, the inflow port 42a is provided in the first side wall 44 as illustrated. The inflow tube 42 is a connecting pipe fitted to the inflow port 42a and is configured such that a pipe or a tube connector for connection to the fluid sterilization apparatus 20 can be mounted.

The inflow port 42a and the inflow tube 42 are arranged such that the direction from the first gap 52 toward the inflow port 42a and the longitudinal direction of the inflow tube 42 are not on the same straight line. More specifically, the inflow port 42a is located at a position shifted from the first gap 52 in the axial direction, and the inflow tube 42 extends in a direction (the radial direction, in the illustrated example) intersecting the direction from the first gap 52 toward the inflow port 42a. This arrangement mitigates an impact that results in variation in the flow rate depending on the position in the circumferential direction of the first gap 52. More specifically, the arrangement mitigates an impact that results in the flow F1 of the fluid flowing in the first gap 52 at a position relatively near the inflow port 42a being faster and the flow F2 at a position relatively far from the inflow port 42a being slower due to the direction of the flow in the inflow tube 42.

The first light source 28 is provided inside the first light source chamber 40 and is arranged to output ultraviolet light toward the opening of the first end 32. It is preferable that the first light source 28 be provided in the vicinity of the first end 32 and be arranged such that the entirety of the ultraviolet light in the range of directivity angle half-power beam width φ of the first light source 28 is incident into the processing passage 36. More specifically, denoting the distance from the light emission part of the first light source 28 to the first end 32 by 1, and denoting the diameter of the opening of the first end 32 by d, it is preferable that the first light source 28 be arranged such that $1 \leq d/(2 \tan(\varphi/2))$.

The first light source 28 includes a first light emitting device 54 and a first substrate 56. The first light emitting device 54 is a light emitting diode (LEDs) configured to emit ultraviolet light, and the central wavelength or peak wavelength thereof is included in a range of about 200 nm~350 nm. It is preferable that the first light emitting device 54 emit ultraviolet light near a wavelength range of 260 nm~290 nm having a high sterilizing efficiency. Such an ultraviolet LED is exemplified by an aluminum gallium nitride (AlGaN) based LED.

Figure 4:
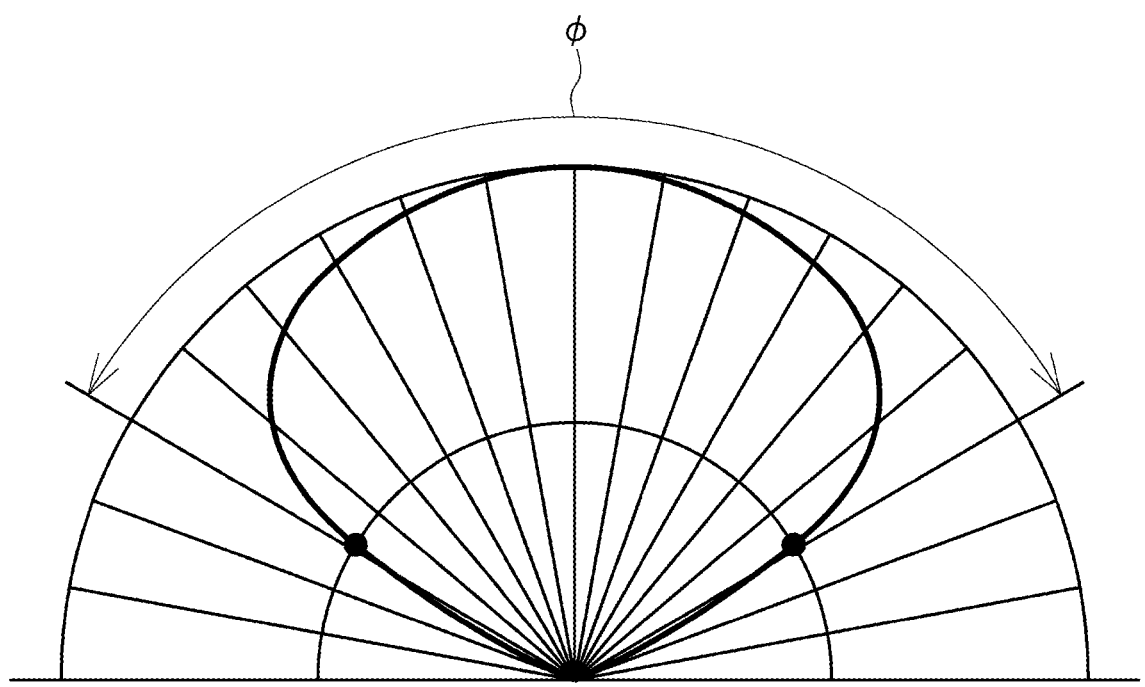
FIG. 4 is a graph showing the light distribution characteristic of the first light emitting device.

FIG. 4 is a graph showing the light distribution characteristic of the first light emitting device 54. The first light emitting device 54 is an LED having a predetermined directivity angle or light distribution angle. As shown in the figure, the first light emitting device 54 is a wide light-distribution LED characterized by a directivity angle half-power beam width φ of about 120°. The first light emitting device 54 with such a specification is exemplified by a surface mount device (SMD) type LED characterized by a high output intensity. The first light emitting device 54 is arranged on the central axis A of the flow passage tube 22 and is mounted on the first substrate 56 so as to face the first window 50. The first substrate 56 is made by using a highly exoergic member. For example, copper (Cu), aluminum (Al), or the like is used as a base material. The heat generated by the first light emitting device 54 is dissipated via the first substrate 56.

The second housing 26 is configured in a manner similar to that of the first housing 24. The second housing 26 is provided to encircle the second end 34 and defines a second straightening chamber 58 and a second light source chamber 60. The second housing 26 has a second side wall 62, a second inner end wall 64, and a second outer end wall 66.

The second side wall 62 is a cylindrical member extending from the second inner end wall 64 to the second outer end wall 66 in the axial direction and is provided at a position coaxial with the central axis A of the flow passage tube 22. The second inner end wall 64 is an annular member provided at a position axially inward from the second end 34 and is fixed to the outer circumferential surface 22c of the flow passage tube 22. The second outer end wall 66 is a disc-shaped member provided at a position axially outward from the second end 34. The second inner end wall 64 and the second outer end wall 66 are provided at positions axially facing each other, sandwiching the second end 34.

A second window 68 for transmitting the ultraviolet light from the second light source 30 is provided inside the second housing 26. The second window 68 partitions the interior of the second housing 26 into the second straightening chamber 58 and the second light source chamber 60. The second straightening chamber 58 is an area defined by the second side wall 62, the second inner end wall 64, and the second window 68 and is an area provided annularly to encircle the second end 34 from outside in the radial direction. The second light source chamber 60 is an area defined by the second side wall 62, the second outer end wall 66, and the second window 68 and is provided with the second light source 30.

The second window 68 is a member that faces the second end 34 in the axial direction and is provided in the vicinity of the second end 34 so as to provide a second gap 70 of a small dimension relative to the second end 34. For example, the second gap 70 is formed to be narrower than the cross-sectional area of flow of the second straightening chamber 58. It is preferable that the second window 68 be provided such that the dimension of the second gap 70 is uniform over the entire circumference of the second end 34. It is also preferable that the end face of the second end 34 and the face of the second window 68 facing the end face of the second end 34 are substantially parallel.

The second housing 26 is provided with an outflow port 72a and an outflow tube 72. The outflow port 72a is a communication port through which the fluid irradiated with ultraviolet light in the processing passage 36 flows out and is provided at a position communicating with the second straightening chamber 58. The outflow tube 72 is a connecting pipe fitted to the outflow port 72a. The outflow port 72a and the outflow tube 72 are arranged such that the direction from the second gap 70 toward the outflow port 72a and the longitudinal direction of the outflow tube 72 are not on the same straight line. More specifically, the outflow port 72a is located at a position shifted from the second gap 70 in the axial direction, and the outflow tube 72 extends in a direction (the radial direction, in the illustrated example) intersecting the direction from the second gap 70 toward the outflow port 72a. The arrangement mitigates an impact that results in the flow F3 of the fluid flowing in the second gap 70 at a position relatively near the outflow port 72a being faster and the flow F4 at a position relatively far from the outflow port 72a being slower due to the direction of the flow in the outflow tube 72.

The second light source 30 is arranged inside the second light source chamber 60 and is arranged to output ultraviolet light toward the opening of the second end 34. As in the case of the first light source 28, it is preferable that the second light source 30 be provided in the vicinity of the second end 34 and be arranged such that the entirety of the ultraviolet light in the range of directivity angle half-power beam width φ of the second light source 30 is incident into the processing passage 36. The second light source 30 is configured in a manner similar to that of the first light source 28 and includes a second light emitting device 74 and a second substrate 76.

With the above-described configuration, the fluid sterilization apparatus 10 irradiates the fluid flowing in the processing passage 36 with the ultraviolet light from the first light source 28 and the second light source 30 so as to sterilize the fluid. The fluid subject to the treatment flows from the first end 32 into the processing passage 36 via the inflow tube 42, the inflow port 42a, the first straightening chamber 38, and the first gap 52. The fluid flowing in the processing passage 36 is straightened such that, for example, the flow rate $v_1$ near the center of the cross-section perpendicular to the axial direction is relatively high and the flow rate $v_2$ near the inner circumferential surface 22b is relatively low. The fluid passing through the processing passage 36 flows out from the second end 34 via the second gap 70, the second straightening chamber 58, the outflow port 72a, and the outflow tube 72.

In this process, the first straightening chamber 38 straightens the flow of the fluid flowing in via the inflow tube 42 and the inflow port 42a and conditions the flow of the fluid flowing into the processing passage 36 in a radial fashion (radially inward) from different circumferential positions via the first gap 52 to be uniform. By conditioning the flow in the first gap 52 to be uniform, the first straightening chamber 38 straightens the flow from the position in the vicinity of the first end 32 to the processing passage 36. Similarly, the second straightening chamber 58 straightens the flow of the fluid flowing out via the outflow port 72a and the outflow tube 72 and conditions the flow of the fluid flowing out from the processing passage 36 in a radial fashion (radially outward) via the second gap 70 to be uniform. By conditioning the flow in the second gap 70 to be uniform, the second straightening chamber 58 maintains the flow in the processing passage 36 in a straightened state as far as the position in the vicinity of the second end 34.

The first light source 28 and the second light source 30 irradiate the fluid straightened as described above and flowing in the processing passage 36 with ultraviolet light. The first light source 28 and the second light source 30 have an intensity distribution as shown in FIG. 4 in which the intensity near the center is high and the intensity radially outward is low and so can radiate ultraviolet light with an intensity conforming to the flow rate distribution in the processing passage 36. In other words, the light sources can radiate high-intensity ultraviolet light near the center where the flow rate is high and radiate low-intensity ultraviolet light at positions radially outward where the flow rate is low. As a result, it is ensured that the amount of energy of ultraviolet light affecting the fluid passing through the processing passage 36 is uniform regardless of the radial position of passage of the fluid. Consequently, the entirety of the fluid flowing in the processing passage 36 is irradiated with ultraviolet light of a predetermined amount of energy or higher so that the sterilizing effect on the entirety of the fluid is increased.

Further, in the fluid sterilization apparatus 20 according to the embodiment, the first straightening chamber 38 and the second straightening chamber 58 are provided at the respective ends of the flow passage tube 22. Therefore, a disturbance in the flow produced in the processing passage 36 can be inhibited more successfully than in the fluid sterilization apparatus 10 according to the first embodiment. In particular, it is easy to maintain the straightened state even when the average flow rate of the fluid flowing in the processing passage 36 is increased in order to increase the processing capability of the fluid sterilization apparatus 20. Thus, the embodiment allows the ultraviolet light to effectively affect the fluid flowing in a less disturbed state than in the related art, thereby increasing the sterilization effect.

According to the embodiment, the majority of the ultraviolet light output from the first light source 28 and the second light source 30 is conditioned to be incident on the interior of the flow passage tube 22, and the ultraviolet light incident on the interior of the flow passage tube 22 propagates in the axial direction, repeatedly reflected by the inner circumferential surface 22b of the flow passage tube 22. Consequently, the ultraviolet light output from the first light source 28 and the second light source 30 can be efficiently used to increase the sterilization efficiency. Further, the projections 32a and 34a are provided in the first end 32 and the second end 34 in a range that does not block the incidence of the ultraviolet light, ensuring that a larger portion of the ultraviolet light is contained inside the flow passage tube 22 than in the related art so that the efficiency of using the ultraviolet light is increased.

According to the embodiment, the majority of the ultraviolet light output from the first light source 28 and the second light source 30 is contained inside the flow passage tube 22 so that the amount of ultraviolet light leaking outside the flow passage tube 22 is reduced. Since the first housing 24 and the second housing 26 are made of a material that does not reflect ultraviolet light so much, the ultraviolet light is prevented from propagating by being reflected by the inner surface of the first housing 24 or the second housing 26 and from leaking outside the fluid sterilization apparatus 20 via the inflow tube 42 or the outflow tube 72. This enhances the safety of the fluid sterilization apparatus 20 and mitigates an impact that results in the resin tube, connector, etc. connected to the inflow tube 42 and the outflow tube 72 being irradiated with ultraviolet light and degraded accordingly.

Figure 5:
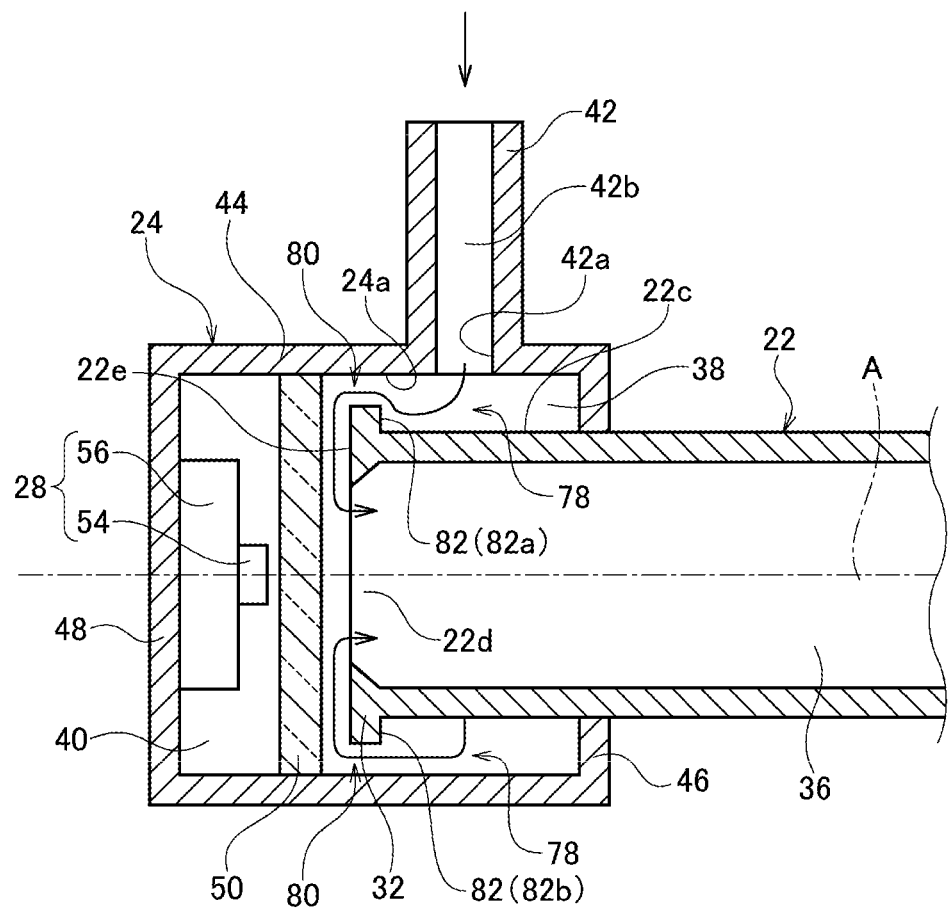
FIG. 5 is an enlarged view of the vicinity of the first straightening chamber of FIG. 3.

In the fluid sterilization apparatus 20 according to this embodiment, a further narrow passage is provided in the first straightening chamber 38 and the second straightening chamber 58. FIG. 5 is an enlarged view of the vicinity of the first straightening chamber 38 of FIG. 3. Illustration of a convex part for forming a narrow passage is omitted in FIG. 3.

As shown in FIG. 5, the fluid sterilization apparatus 20 includes: the flow passage tube 22 in which the processing passage 36 where the passing fluid is sterilized is formed; the first light source 28 that irradiates the processing passage 36 with ultraviolet light; an inflow passage 42b formed in a direction that intersects the outer circumferential surface 22c of the flow passage tube 22; and a communication passage 78 that causes the inflow passage 42b and the processing passage 36 to communicate with each other. The communication passage 78 has a narrow passage 80 in the middle of a path from the inflow passage 42b toward an opening 22d of the first end 32 of the flow passage tube 22, the narrow passage 80 being narrower than a passage toward the inflow passage.

The narrow passage 80 straightens the flow by blocking a direct flow from the inflow passage 42b toward the first end 32 of the flow passage tube 22 and distributing the flow elsewhere. In particular, the narrow passage 80 inhibits a disturbance in the flow from being produced near the first end 32 of the flow passage tube 22, which is close to the light source, thereby straightening the flow.

The communication passage 78 is formed between the flow passage tube 22 and the first housing 24 that covers the opening 22d of the first end 32 of the flow passage tube 22 and the outer circumferential surface 22c near the opening 22d. Thus, by designing the shape of a plurality of members properly, the communication passage 78 can be formed as a gap between the plurality of members.

For example, in the flow passage tube 22 shown in FIG. 5, a convex part 82 is formed more toward the opening 22d than the portion of the outer circumferential surface 22c of the flow passage tube 22 facing the inflow passage 42b. The narrow passage 80 is formed between the convex part 82 and an inner circumferential surface 24a of the first housing 24. In this way, the narrow passage 80 can be formed by forming a simple shape in the flow passage tube 22.

The convex part 82 according to this embodiment is formed annularly in the circumferential direction of the outer circumferential surface 22c of the flow passage tube 22. This can condition the flow of the fluid to be relatively uniform over the entire outer circumference of the flow passage tube 22. The convex part 82 may not necessarily be formed over the entire circumference but may be formed in part. The height of the convex part may vary in part. For example, the flow rate of the fluid at a position relatively far from the inflow port 42a tends to be slow, as described above. Associated with this, the height of a convex part 82b formed in the communication passage 78 opposite to the inflow port 42a (toward the bottom of FIG. 5) may be larger than the height of a convex part 82a formed in the communication passage 78 near the inflow port 42a. This allows the narrow passage 80 between the convex part 82b and the inner circumferential surface 24a of the first housing 24 to straighten the flow by blocking a direct flow from the inflow passage 42b toward the first end 32 of the flow passage tube 22 and distributing the flow elsewhere.

The convex part 82 is provided on the outer circumferential surface 22c of the flow passage tube 22 but may be provided on an end face 22e around the opening 22d of the flow passage tube 22. Further, convex parts similar to those of the first straightening chamber 38 may be provided in the second straightening chamber 58.

Figure 6:
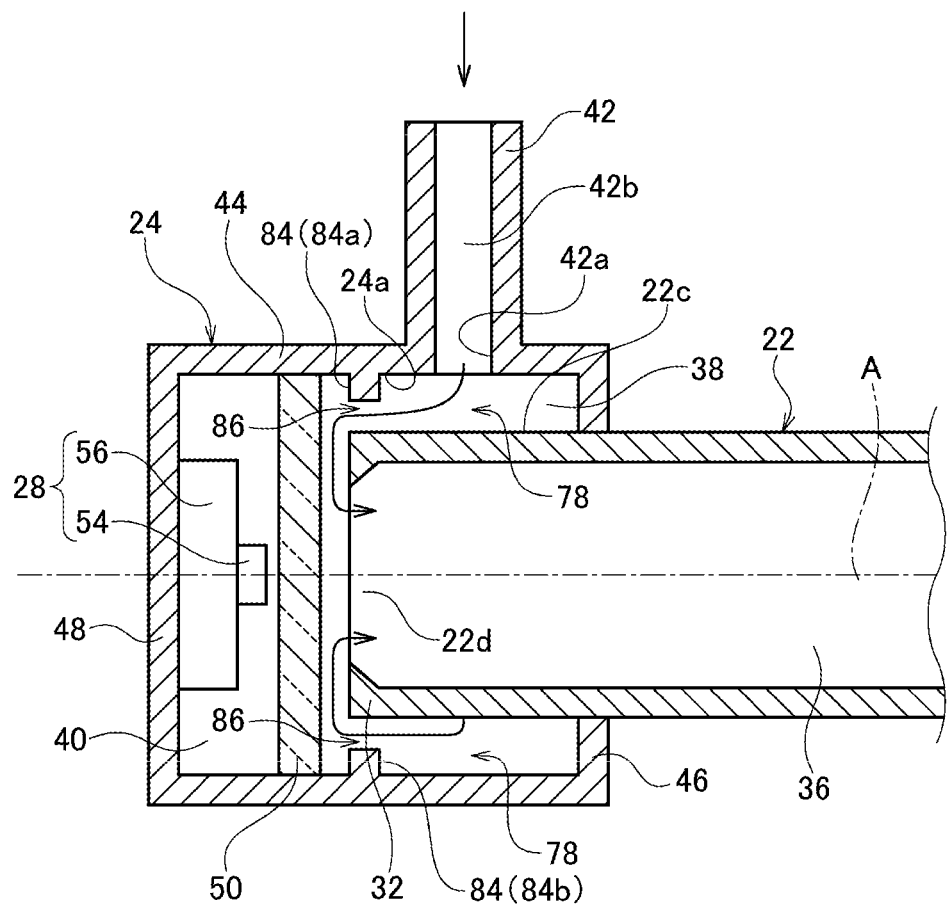
FIG. 6 is an enlarged view of the vicinity of the first straightening chamber of a fluid sterilization apparatus according to a variation of the second embodiment.

FIG. 6 is an enlarged view of the vicinity of the first straightening chamber 38 of a fluid sterilization apparatus according to a variation of the second embodiment.

As shown in FIG. 6, the first housing 24 is configured such that a convex part 84 is formed more toward opening 22d than an area on the inner circumferential surface 24a of the first housing 24 where the inflow passage 42b is formed, and a narrow passage 86 is formed between the convex part 84 and the outer circumferential surface 22c of the flow passage tube 22. In this way, the narrow passage 86 can be formed by forming a simple shape in the first housing 24.

The convex part 84 according to this embodiment is formed annularly in the circumferential direction of the inner circumferential surface 24a of the first housing 24. This can condition the flow of the fluid to be relatively uniform over the entire outer circumference of the flow passage tube 22. The convex part 84 may not necessarily be formed over the entire circumference but may be formed in part. The height of the convex part may vary in part. For example, the flow rate of the fluid at a position relatively far from the inflow port 42a tends to be slow, as described above. Associated with this, the height of a convex part 84b formed in the communication passage 78 opposite to the inflow port 42a (toward the bottom of FIG. 6) may be larger than the height of a convex part 84a formed in the communication passage 78 near the inflow port 42a. This allows the narrow passage 86 between the convex part 84b and the outer circumferential surface 22c of the flow passage tube 22 to straighten the flow by blocking a direct flow from the inflow passage 42b toward the first end 32 of the flow passage tube 22 and distributing the flow elsewhere.

Third Embodiment

Figure 7:
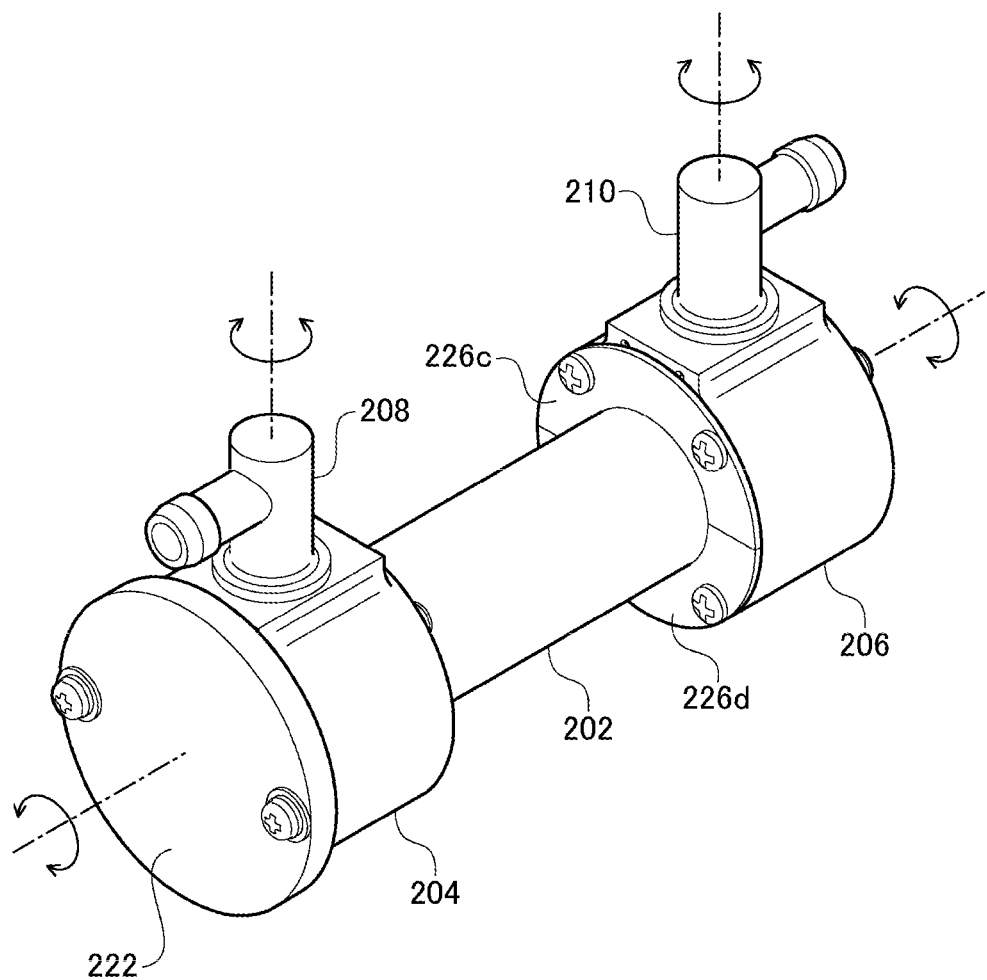
FIG. 7 is a perspective view of a fluid sterilization apparatus according to a third embodiment.
Figure 8:
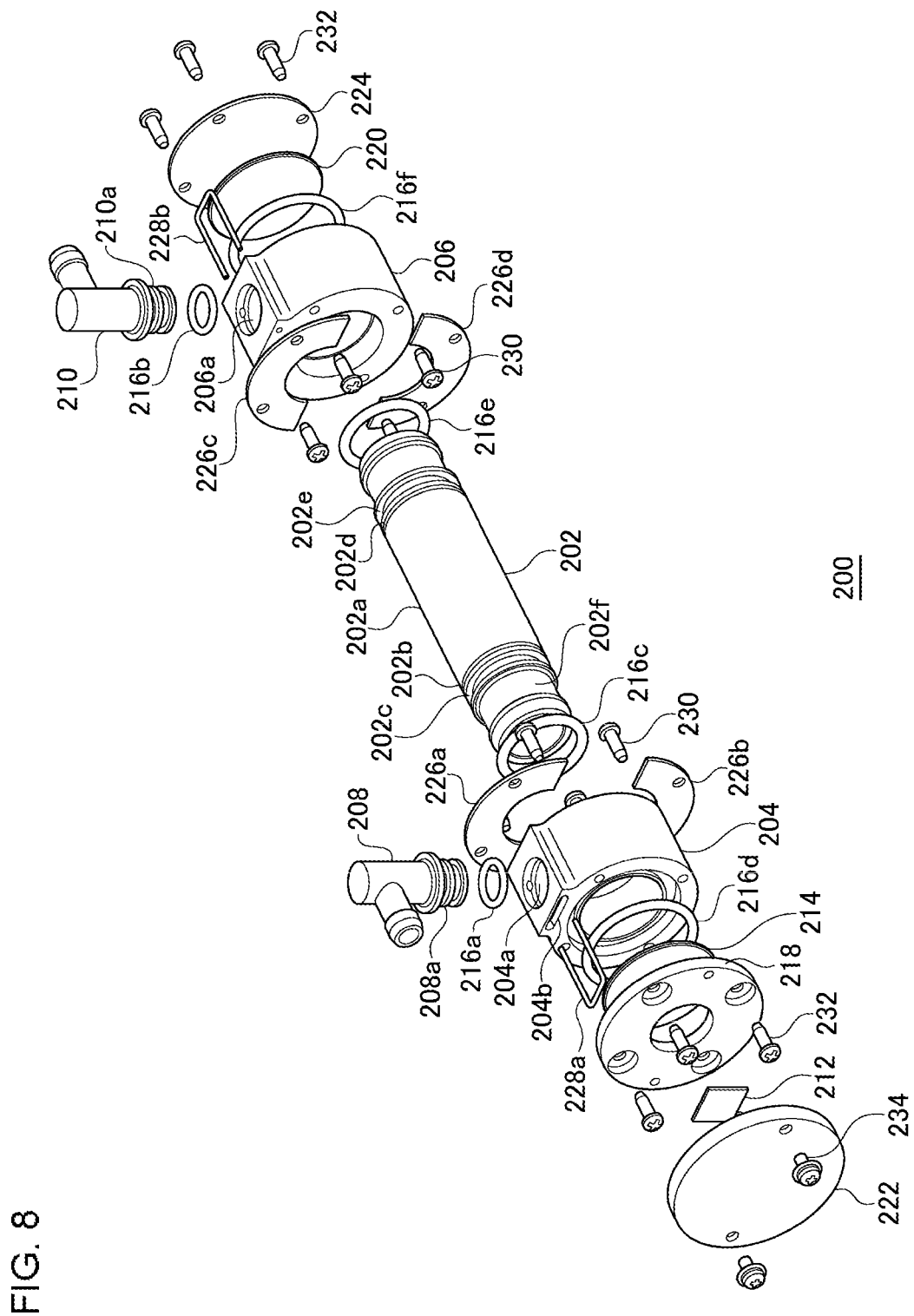
FIG. 8 is an exploded perspective view of the fluid sterilization apparatus according to the third embodiment.
Figure 9:
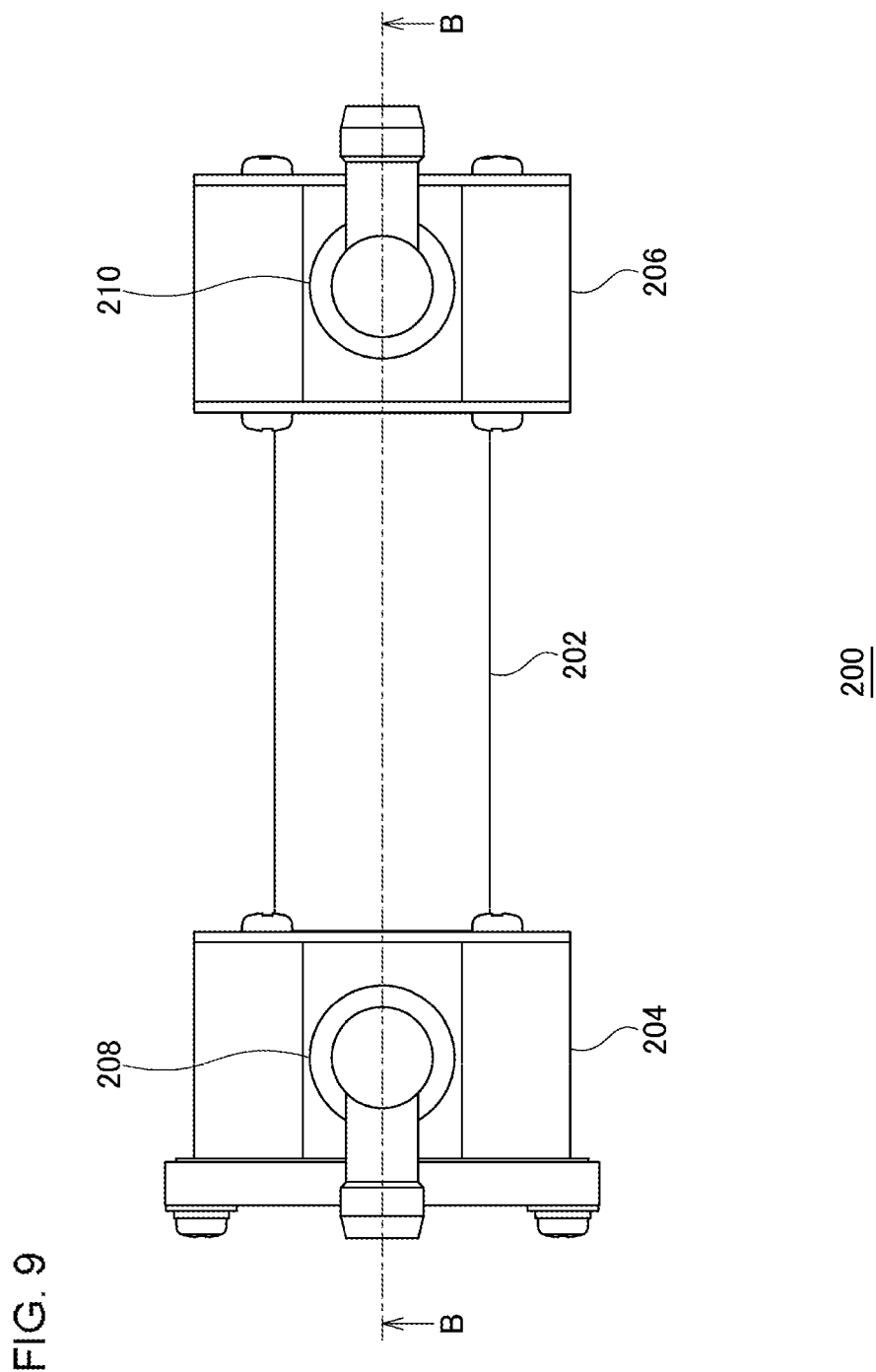
FIG. 9 is a top view of the fluid sterilization apparatus according to the third embodiment.
Figure 10:
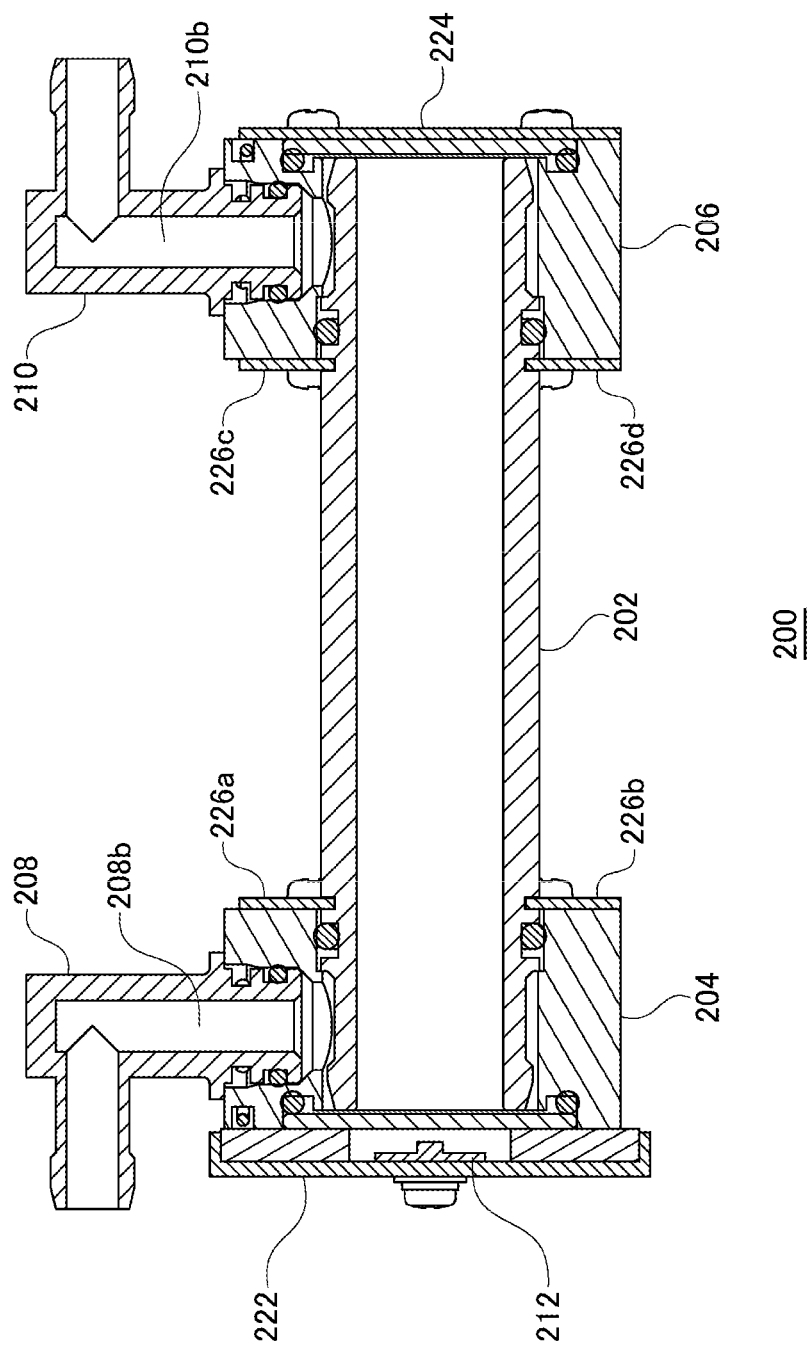
FIG. 10 shows a B-B section of the fluid sterilization apparatus shown in FIG. 9.

FIG. 7 is a perspective view of a fluid sterilization apparatus according to a third embodiment. FIG. 8 is an exploded perspective view of the fluid sterilization apparatus according to the third embodiment. FIG. 9 is a top view of the fluid sterilization apparatus according to the third embodiment. FIG. 10 shows a B-B section of the fluid sterilization apparatus shown in FIG. 9.

A fluid sterilization apparatus 200 according to this embodiment includes a flow passage tube 202, a first housing 204, a second housing 206, an inflow tube 208, an outflow tube 210, a light source 212, a window member 214, O rings 216a~216f, a ring member 218, a plate 220, cover members 222 and 224, semi-ring shaped plates 226a~226d, U-shaped retaining pins 228a and 228b.

A plurality of grooves (convex parts) or an elongated protrusion is formed on the outer circumferential surface of the flow passage tube 202 in the circumferential direction. The first housing 204 is a cylindrical member, and an opening 204a in which the inflow tube 208 is mounted is formed on a side of the first housing 204. The inflow tube 208 is inserted via the O ring 216a into the first housing 204 as far as a predetermined position. Further, the inflow tube 208 is fixed and retained at a predetermined position as the retaining pin 228a inserted from a slit 204b formed on the axial end face of the first housing 204 is engaged with a groove 208a formed at the base of the inflow tube 208.

Similarly, the second housing 206 is a cylindrical member, and an opening 206a in which the outflow tube 210 is mounted is formed on a side of the second housing 206. The outflow tube 210 is inserted via the O ring 216b into the second housing 206 as far as a predetermined position. Further, the outflow tube 210 is fixed and retained at a predetermined position as the retaining pin 228b inserted from a slit (not shown) formed on the axial end face of the second housing 206 is engaged with a groove 210a formed at the base of the outflow tube 210.

The flow passage tube 202 is inserted from one opening of the first housing 204 in the axial direction as far as a predetermined position while the two semi-ring shaped plates 226a and 226b are mounted in an annular slit 202b formed on an outer circumferential surface 202a and an O ring 216c is mounted in an annular concave groove 202c. Subsequently, the flow passage tube 202 is positioned and fixed to the first housing 204 as the two semi-ring shaped plates 226a and 226b are screwed to the first housing 204 by a screw 230. Further, the other opening of the first housing 204 in the axial direction is sealed by a window member 214 via the O ring 216d. The ring member 218 is screwed to the first housing 204 by a screw 232, pressing the window member 214.

The cover member 222 is screwed to the ring member 218 by a screw 234 while the light source 212 is mounted at a position aligned with the opening of the ring member 218.

Further, the flow passage tube 202 is inserted from one opening of the second housing 206 in the axial direction as far as a predetermined position while the two semi-ring shaped plates 226c and 226d are mounted in an annular slit 202d formed on the outer circumferential surface 202a and an O ring 216e is mounted in an annular concave groove 202e. Subsequently, the flow passage tube 202 is positioned and fixed to the second housing 206 as the two semi-ring shaped plates 226c and 226d are screwed to the second housing 206 by the screw 230. Further, the other opening of the second housing 206 in the axial direction is sealed by a plate 220 via the O ring 216f. The cover member 224 is screwed to the second housing 206 by a screw 232, pressing the plate 220.

Figure 11:
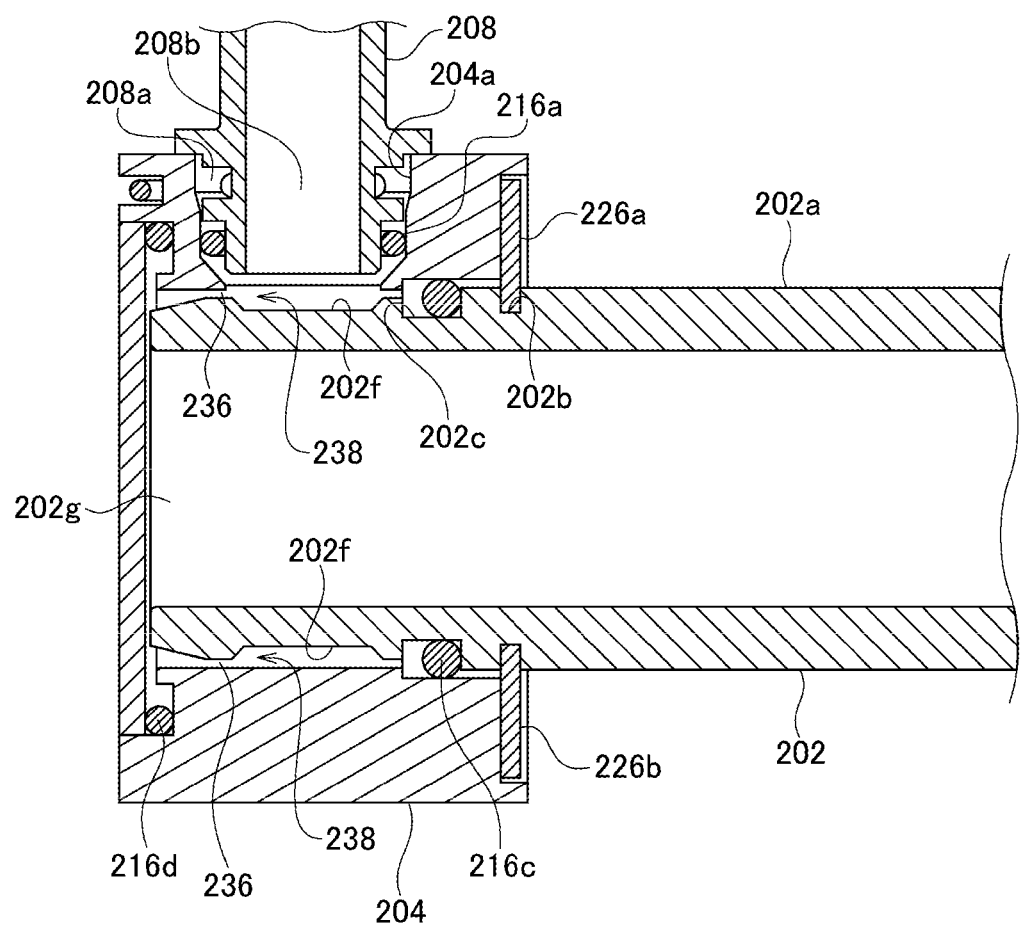
FIG. 11 is an enlarged view schematically showing the vicinity of a portion connecting the inflow tube and the first housing of FIG. 10.

FIG. 11 is an enlarged view schematically showing the vicinity of a portion connecting the inflow tube 208 and the first housing 204 of FIG. 10. The vicinity of a portion connecting the outflow tube 210 and the second housing 206 is configured similarly.

The flow passage tube 202 shown in FIG. 11 is configured such that a concave part 202f is formed in a portion of the outer circumferential surface 202a of the flow passage tube 202 facing an inflow passage 208b. In this way, an area adjacent to the concave part 202f can be configured as a narrow passage 236 by forming a simple shape in the flow passage tube 202.

The concave part 202f according to this embodiment is formed annularly in the circumferential direction of the outer circumferential surface 202a of the flow passage tube 202. This can condition the flow of the fluid over the entire outer circumference of the flow passage tube 202.

The narrow passage 236 is provided more toward an opening 202g of the flow passage tube 202 than the concave part 202f. This can condition the flow of the fluid between the concave part 202f and the opening 202g.

The vicinity of a portion connecting the outflow tube 210 and the second housing 206 is configured similarly.

A description will now be given of a rotary mechanism for the inflow tube 208 in the fluid sterilization apparatus 200. The rotary mechanism for the outflow tube 210 is similar to that of the inflow tube 208.

The inflow tube 208 is mounted in the opening 204a formed on the outer circumferential surface of the first housing 204 such that the inflow tube 208 is rotatable relative to the first housing 204. More specifically, the inflow tube 208 is prevented from being dislodged from the first housing 204 merely by engaging the retaining pin 228a with the groove 208a. In other words, the inflow tube 208 is supported so as to be rotatable relative to the first housing 204 around the center of the opening 204a of the first housing 204. Similarly, the outflow tube 210 is supported so as to be rotatable relative to the second housing 206.

As shown in FIG. 7, the inflow tube 208 and the outflow tube 210 are configured such that the inflow passage 208b and the outflow passage 210b are L-shaped (crank shaped). The inflow tube 208 is configured to be rotatable relative to the first housing 204, and the outflow tube 210 is configured to be rotatable relative to the second housing 206. This configuration allows the orientation of the inflow tube 208 and the outflow tube 210 to be changed depending on the location where the fluid sterilization apparatus 200 is installed. The fluid sterilization apparatus 200 can thus be installed in an orientation in which its performance is easily exhibited. More specifically, the fluid sterilization apparatus 200 cannot exhibit the full performance if bubbles are collected inside, unlike simple pipes in which it is sufficient to cause an ordinary fluid to flow. For this reason, bubbles introduced at the time of installation of the fluid sterilization apparatus 200 need be removed outside before the device is put into operation. This is addressed by filling the device with the fluid at the time of installation while the device is oriented such that bubbles are easily removed. Once bubbles are removed, the orientation of the inflow tube 208 or the outflow tube 210 may be changed so that the tubes are connected to conform to the location of installation.

The fluid sterilization apparatus 200 according to this embodiment is configured such that the first housing 204 and the second housing 206 are mounted at the ends of the flow passage tube 202 so as to be rotatable around the axis of the flow passage tube 202. More specifically, the first housing 204 is prevented from being dislocated by being latched to the flow passage tube 202 by means of the semi-ring shaped plates 226a and 226b but is rotatable in a direction of rotation around the center of the opening 202g of the flow passage tube 202 (see FIG. 7). This allows indirectly changing the orientation of the outflow tube or the inflow tube depending on the location of installation of the fluid sterilization apparatus 200, by rotating the first housing 204 and the second housing 206 relative to the flow passage tube 202. The fluid sterilization apparatus 200 can thus be installed or operated in an orientation in which it can exhibit its performance easily.

As shown in FIGS. 7 through 11, the fluid sterilization apparatus 200 according to this embodiment includes the flow passage tube 202 in which the processing passage where the passing fluid is sterilized is formed; the light source 212 that irradiates the processing passage with ultraviolet light; the inflow passage 208b formed in a direction that intersects the outer circumferential surface 202a of the flow passage tube 202; and a communication passage 238 that causes the inflow passage 208b and the processing passage to communicate with each other. The communication passage 238 has a narrow passage 236 in the middle of a path from the inflow passage 208b toward an opening 202g of one end of the flow passage tube 202, the narrow passage 236 being narrower than a passage toward the inflow passage.

This allows the narrow passage 236 to straighten the flow by blocking a direct flow from the inflow passage 208b toward the one end of the flow passage tube 202 and distributing the flow elsewhere. In particular, the narrow passage 236 inhibits a disturbance in the flow from being produced near the one end of the flow passage tube 202, which is close to the light source, thereby straightening the flow.

Further, the O rings 216a~216f used in the fluid sterilization apparatus 200 are placed at locations in contact with the fluid and so can be irradiated with the ultraviolet light propagating in the fluid. For this reason, the O rings 216a~216f are made of a material containing fluorine to provide the rings with ultraviolet resistance.

The embodiments of the present invention are not limited to those described above and appropriate combinations or replacements of the features of the embodiments are also encompassed by the present invention. The embodiments may be modified by way of combinations, rearranging of the processing sequence, design changes, etc., based on the knowledge of a skilled person, and such modifications are also within the scope of the present invention.

In the third embodiment, the rotary mechanism is described as being provided in a portion connecting the first housing 204 and the second housing 206 of the fluid sterilization apparatus 200 of a dual tube structure with the flow passage tube 202, a portion connecting the first housing 204 with the inflow tube 208, and a portion connecting the second housing 206 with the outflow tube 210, respectively. However, the application of the rotary mechanism is not limited to the dual tube structure. For example, the rotary mechanism may be provided in the fluid sterilization apparatus as shown in FIG. 1.

In the case the rotary mechanism as shown in the third embodiment is provided between the housing and the flow passage tube, it is preferable to provide the narrow passage over the entire circumference of the flow passage tube so that the narrow passage is continuously located in the vicinity of the inflow passage or the outflow passage even when the housing is rotated relative to the flow passage tube.

In the case the rotary mechanism is not provided between the housing and the flow passage tube, on the other hand, the narrow passage be provided only at a side close to the inflow passage or the outflow passage.

In the case a light source is provided only at one end of the flow passage tube as in the case of the fluid sterilization apparatus 200 shown in FIG. 10, the flow toward the light source is stabilized and the sterilization efficiency is improved by causing the fluid to flow in from the other end where a light source is not provided. In other words, the outflow tube 210 may be connected to the first housing 204 where the light source 212 is provided and the inflow tube 208 may be connected to the second housing 206.

The invention claimed is:

1. A fluid sterilization apparatus, comprising:
   a flow passage tube in which a processing passage where a passing fluid is sterilized is formed;
   a light source that irradiates the processing passage with ultraviolet light;
   an inflow passage or an outflow passage formed in a direction that intersects an outer circumferential surface of the flow passage tube; and
   a communication passage that causes the inflow passage or the outflow passage to communicate with the processing passage,
   wherein the communication passage has a narrow passage in the middle of a path from the inflow passage or the outflow passage toward an opening of one end of the flow passage tube, the narrow passage being narrower than a passage toward the inflow passage or the outflow passage,
   wherein the communication passage is formed between the flow passage tube and a housing that covers an opening of the one end of the flow passage tube and the outer circumferential surface near the opening,
   wherein a convex part is formed more toward the opening than a portion of the outer circumferential surface of the flow passage tube facing the inflow passage or the outflow passage, and the narrow passage is formed between the convex part and an inner circumferential surface of the housing, and
   wherein the convex part is formed annularly in a circumferential direction of the outer circumferential surface of the flow passage tube.

2. A fluid sterilization apparatus, comprising:
   a flow passage tube in which a processing passage where a passing fluid is sterilized is formed;
   a light source that irradiates the processing passage with ultraviolet light;
   an inflow passage or an outflow passage formed in a direction that intersects an outer circumferential surface of the flow passage tube; and
   a communication passage that causes the inflow passage or the outflow passage to communicate with the processing passage,
   wherein the communication passage has a narrow passage in the middle of a path from the inflow passage or the outflow passage toward an opening of one end of the flow passage tube, the narrow passage being narrower than a passage toward the inflow passage or the outflow passage,
   wherein the communication passage is formed between the flow passage tube and a housing that covers an opening of the one end of the flow passage tube and the outer circumferential surface near the opening,
   wherein the housing is configured such that a convex part is formed more toward the opening than an area on an inner circumferential surface of the housing where the inflow passage or the outflow passage is formed, and a narrow passage is formed between the convex part and the outer circumferential surface of the flow passage tube, and wherein the convex part is formed annularly in a circumferential direction of the inner circumferential surface of the housing.

3. A fluid sterilization apparatus comprising:

a flow passage tube in which a processing passage where a passing fluid is sterilized is formed;

a light source that irradiates the processing passage with ultraviolet light;

an inflow passage or an outflow passage formed in a direction that intersects an outer circumferential surface of the flow passage tube;

a communication passage that causes the inflow passage or the outflow passage to communicate with the processing passage, and an outflow tube or an inflow tube that forms the outflow passage or the inflow passage, wherein the communication passage has a narrow passage in the middle of a path from the inflow passage or the outflow passage toward an opening of one end of the flow passage tube, the narrow passage being narrower than a passage toward the inflow passage or the outflow passage, wherein the communication passage is formed between the flow passage tube and a housing that covers an opening of the one end of the flow passage tube and the outer circumferential surface near the opening, and the outflow tube or the inflow tube is mounted on an opening formed on an outer circumferential surface of the housing and is supported so as to be rotatable relative to the housing around a center of the opening.

4. A fluid sterilization apparatus, comprising:

a flow passage tube in which a processing passage where a passing fluid is sterilized is formed;

a light source that irradiates the processing passage with ultraviolet light;

an inflow passage or an outflow passage formed in a direction that intersects an outer circumferential surface of the flow passage tube; and a communication passage that causes the inflow passage or the outflow passage to communicate with the processing passage, wherein the communication passage has a narrow passage in the middle of a path from the inflow passage or the outflow passage toward an opening of one end of the flow passage tube, the narrow passage being narrower than a passage toward the inflow passage or the outflow passage, wherein the communication passage is formed between the flow passage tube and a housing that covers an opening of the one end of the flow passage tube and the outer circumferential surface near the opening, and wherein the housing is mounted on one end of the flow passage tube such that the housing is rotatable around a center of an opening of the flow passage tube.

\* \* \* \* \*